United States Patent
Shinada et al.

(10) Patent No.: US 8,970,221 B2
(45) Date of Patent: Mar. 3, 2015

(54) DISCHARGE IONIZATION CURRENT DETECTOR

(75) Inventors: Kei Shinada, Uji (JP); Shigeyoshi Horiike, Uji (JP); Takahiro Nishimoto, Soraku-gun (JP)

(73) Assignee: Shimadzu Corporation, Kyoto-Shi (JP)

( * ) Notice: Subject to any disclaimer, the term of this patent is extended or adjusted under 35 U.S.C. 154(b) by 687 days.

(21) Appl. No.: 13/010,166

(22) Filed: Jan. 20, 2011

(65) Prior Publication Data

US 2011/0187379 A1     Aug. 4, 2011

(30) Foreign Application Priority Data

Feb. 1, 2010 (JP) ................................. 2010-020451

(51) Int. Cl.
*G01N 27/62* (2006.01)
*G01N 27/70* (2006.01)
*G01N 27/68* (2006.01)

(52) U.S. Cl.
CPC ............... *G01N 27/70* (2013.01); *G01N 27/62* (2013.01); *G01N 27/68* (2013.01)
USPC .......................................... 324/464; 324/459

(58) Field of Classification Search
CPC ........ G01N 27/62; G01N 27/68; G01N 27/70
USPC ................................................ 324/464, 468
See application file for complete search history.

(56) References Cited

U.S. PATENT DOCUMENTS

| 4,266,196 | A | 5/1981 | Kawazoe et al. | |
|---|---|---|---|---|
| 5,394,092 | A | 2/1995 | Wentworth et al. | 324/464 |

(Continued)

FOREIGN PATENT DOCUMENTS

| EP | 0046699 A2 * | 3/1982 |
|---|---|---|
| JP | 2005300288 A | 10/2005 |
| WO | WO 2009/119050 A1 | 10/2009 |

OTHER PUBLICATIONS

Japanese language office action dated Apr. 2, 2013 and its English language translation issued in corresponding Japanese application 2010020451 cites the foreign patent document listed above.

(Continued)

*Primary Examiner* — Patrick Assouad
*Assistant Examiner* — Hoang X Nguyen
(74) *Attorney, Agent, or Firm* — Morgan, Lewis & Bockius LLP (57) ABSTRACT

A discharge ionization current detector capable of supplying plasma gas in large quantity to stabilize plasma simultaneously with lowering the sample dilution ratio to improve detection sensitivity is provided. A gas supply pipe 7 for supplying a plasma gas, which also functions as a dilution gas, is connected to a point near the connecting section of a first gas passage 3 having electrodes 4-6 for plasma generation and a second gas passage having electrodes 16 and 17 for ion detection. A first gas discharge pipe 8 is connected to the other end of the first gas passage 3, and a second gas discharge pipe 13 is connected to the other end of the second gas passage 11. Flow controllers 9 and 14 are provided in the gas discharge pipes 8 and 13, respectively. The flow rate of the gas passing through a plasma generation area and that of the gas passing through an ion current detection area can be independently regulated. Therefore, for example, it is possible to increase the former flow rate to stabilize the plasma and simultaneously decrease the latter flow rate to enhance the detection sensitivity for a low-concentration sample.

9 Claims, 4 Drawing Sheets

(56) References Cited

U.S. PATENT DOCUMENTS 5,892,364 A * 4/1999 Monagle ................ 324/464
2004/0178800 A1 * 9/2004 Stearns et al. ............. 324/464

OTHER PUBLICATIONS

Kei Shinada et al., "Excited ionization Current Detector for Gas Chromatography by Atmospheric Pressure Microplasma (II)", The 55th Spring Meeting, 2008 of the Japan Society of Applied Physics and Related Societies 28p-T-4.

Kei Shinada et al.., "Excited Ionization Current Detector for Gas Chromatography by Atmospheric Pressure Microplasma" The 69th Annual Meeting of Japan Society of Applied Physics in 2008 Autumn.

Chinese language office action dated Dec. 20, 2012 and its English language translation issued in corresponding Chinese application 201110034522 cites the U.S. patent listed above.

Chinese Office Action dated Sep. 5, 2013 for corresponding Chinese Patent App. No. 201110034522.X.

English translation of "Reason for Rejection" for Chinese Office Action dated Sep. 5, 2013 for corresponding Chinese Patent App. No. 201110034522.X.

Examination Report Received for Chinese Patent Application No. 201110034522.X, mailed on Aug. 18, 2014, 8 pages (2 pages of English Translation and 6 pages Of Official Copy).

Chinese Office Action dated Feb. 21, 2014 for corresponding Chinese Patent Application No. 201110034522.X, English translation of "Reason for Rejection".

* cited by examiner

DISCHARGE IONIZATION CURRENT DETECTOR

The present invention relates to a discharge ionization current detector primarily suitable as a detector for a gas chromatograph (GC), and more specifically to a discharge ionization current detector using a low-frequency barrier discharge.

BACKGROUND OF THE INVENTION

As the detector for a gas chromatograph, various types of detectors have conventionally been proposed and practically applied, such as a thermal conductivity detector (TCD), electron capture detector (ECD), flame ionization detector (FID), flame photometric detector (FPD) and flame thermionic detector (FTD). Among those detectors, the FID is most widely used, particularly for the purpose of detecting organic substances. The FID is a device that ionizes sample components in a sample gas by hydrogen flame and detects the resultant ion current. It can attain a wide dynamic range of approximately six orders of magnitude. However, the FID has the following drawbacks: (1) Its ionization efficiency is low, so that its minimum detectable amount is not sufficiently low. (2) Its ionization efficiency for alcohols, aromatic substances and chlorine substances is low. (3) It requires hydrogen, which is a highly hazardous substance; therefore, an explosion-proof apparatus or similar kind of special equipment must be provided, which makes the entire system more difficult to operate.

On the other hand, as a detector capable of high-sensitivity detection of various compounds from inorganic substances to low-boiling organic compounds, a pulsed discharge detector (PDD) has conventionally been known (for example, refer to U.S. Pat. No. 5,394,092). In the PDD, the molecules of helium or another substance are excited by a high-voltage pulsed discharge. When those molecules return from the excited state to the ground state, they generate optical energy. This optical energy is utilized to ionize a molecule to be analyzed, and an ion current produced by the generated ions is detected to obtain a detection signal corresponding to the amount (concentration) of the molecule to be analyzed.

In most cases, the PDD can attain higher ionization efficiencies than the FID. For example, the ionization efficiency of the FID for propane is no higher than 0.0005%, whereas the PDD can achieve a level as high as 0.07[%]. Despite this advantage, the dynamic range of the PDD is not as wide as that of the FID; the fact is that the former is one or more digits lower than the latter. This is one of the reasons why the PDD is not as widely used as the FID.

The most probable constraining factors for the dynamic range of the conventional PDD are the unstableness of the plasma created for the ionization and the periodic fluctuation of the plasma state. To solve this problem, a discharge ionization current detector has been proposed (for example, refer to U.S. Pat. No. 5,892,364). This detector uses a low-frequency AC-excited dielectric barrier discharge (which is hereinafter referred to as the low-frequency barrier discharge) to create a stable and steady state of plasma. The plasma created by the low-frequency barrier discharge is non-equilibrium atmospheric pressure plasma, which does not become hot so easily as the plasma created by the radio-frequency discharge. Furthermore, the periodic fluctuation of the plasma, which occurs due to the transition of the voltage application state if the plasma is created by the pulsed high-voltage excitation, is prevented, so that a stable and steady state of plasma can be easily obtained. Based on these findings, the present inventors have conducted various kinds of research on the discharge ionization current detector using a low-frequency barrier discharge and made many proposals on this technique (for example, refer to the following documents: International Publication No. WO2009/119050; Shinada et al., "Taikiatsu Maikuro-purazuma Wo Mochiita Gasu Kuromatogurafu You Ion-ka Denryuu Kenshutsuki (Excited Ionization Current Detector for Gas Chromatography by Atmospheric Pressure Microplasma)", *Extended Abstracts of 55th Meeting of Japan Society of Applied Physics and Related Societies in 2008 Spring*; and Shinada et al., "Taikiatsu Maikuro-purazuma Wo Mochiita Gasu Kuromatogurafu You Ion-ka Denryuu Kenshutsuki (II) (Excited Ionization Current Detector for Gas Chromatography by Atmospheric Pressure Microplasma: Part II)", *Extended Abstracts of 69th Annual Meeting of Japan Society of Applied Physics in 2008 Autumn*).

As explained previously, the low-frequency barrier discharge creates a stable plasma state and is also advantageous for noise reduction. However, it has the following problem.

In the discharge ionization current detector, the sample gas is normally mixed with a plasma gas and the ionization of the sample occurs in this mixed gas. In this process, it is preferable to supply the plasma gas at a high flow rate to improve the plasma's stability and the ionization efficiency. This is primarily because a higher flow rate of the plasma gas results in a larger amount of heat radiation from the electrode (which is heated by the plasma), thus preventing the electrode from being overheated and thereby damaged. The higher flow rate also contributes to a rapid removal of impurities released from the electrode and the inner wall of conduit lines, thus suppressing their influences. On the other hand, the plasma gas also acts as a diluent gas for the sample gas. From this point of view, the flow rate of the plasma gas should be lowered to improve the detection sensitivity of the sample components. Therefore, to make the detector applicable for various purposes, the flow rate of the plasma gas needs to be moderately selected to realize an appropriate trade-off between the plasma stability and the detection sensitivity. This means that the detector cannot be used for extreme cases, such as the detection of an extremely small amount of component.

In the case of a portable GC system designed for field analyses aimed at detecting volatile organic compounds (VOC) or similar substances, a small gas cylinder is used as the gas supply source. Therefore, the plasma gas needs to be supplied at the lowest possible flow rate during the detecting operation. On the other hand, when the measurement is performed for a high-concentration sample, lowering the flow rate of the plasma gas may lead to inadequate dilution of the sample, with the result that the sample's concentration falls outside the linear range of the detection sensitivity and hence cannot be correctly measured.

Thus, in the case of the conventional discharge ionization current detector, since the detectable range of the sample concentration significantly depends on the flow rate of the plasma gas, it is difficult for any single device to be used for various purposes and usages as well as for various samples having a broad range of concentrations, so that it is necessary to prepare a dedicated device for each different demand. The present invention has been developed in view of this point, and its objective is to provide a discharge ionization current detector applicable to a broad range of sample concentration and capable of performing an optimal measurement depending on the purpose, usage and conditions of the measurement.

SUMMARY OF THE INVENTION

A first aspect of the present invention aimed at solving the previously described problem is a discharge ionization current detector including: a first gas passage for passing a plasma gas therethrough; a plasma generator for generating a dielectric barrier discharge in the first gas passage by a low-frequency alternating electric field to create plasma from the plasma gas; a second gas passage continuously extending from the first gas passage; and a current detector for detecting, in the second gas passage, an ion current due to a sample component in a sample gas ionized by the action of the plasma, the discharge ionization current detector including:

a) a plasma-gas supply port and a plasma-gas discharge port for passing a plasma gas through the first gas passage, the plasma-gas supply port being provided in the first gas passage on one side of a plasma generation area where the plasma is generated by the plasma generator, and the plasma-gas discharge port being provided in the first gas passage on the other side of the plasma generation area;

b) a sample-gas injector for supplying a sample gas into the second gas passage;

c) a diluent-gas supply port and a diluent-gas discharge port for passing the sample gas through the second gas passage after diluting the sample gas, the diluent-gas supply port being provided in the second gas passage on one side of a current detection area where the ion current is detected by the current detector, and the diluent-gas discharge port being provided in the second gas passage on the other side of the current detection area; and d) flow controllers respectively provided at the plasma-gas supply port and the diluent-gas supply port, or at the plasma-gas discharge port and the diluent-gas discharge port.

Examples of the plasma gas include helium, argon, nitrogen, neon, xenon, and any mixture of two or more of them. These gases can also be used as the diluent gas.

The plasma generator may include: a pair of discharge electrodes exposed to the inside of the first gas passage, at least one discharge electrode being coated with a dielectric material; and an AC power source for applying, to the discharge electrodes, a low-frequency AC voltage having a frequency range from 1 kHz to 100 kHz.

In a first mode of the first aspect of the present invention, a common port functioning as both the plasma-gas supply port and the diluent-gas supply port is provided at a connecting section of the first gas passage and the second gas passage, and the flow controllers are respectively provided at the plasma-gas discharge port and the diluent-gas discharge port.

In a second mode of the first aspect of the present invention, a common port functioning as both the plasma-gas discharge port and the diluent-gas discharge port is provided at a connecting section of the first gas passage and the second gas passage, and the flow controllers are respectively provided at the plasma-gas supply port and the diluent-gas supply port.

In the first mode, when a flow of gas supplied through the common port functioning as the plasma-gas supply port and diluent-gas supply port reaches the vicinity of the connecting section of the first gas passage and the second gas passage, the gas is separated into the first and second gas passages, forming two streams of gas flowing toward the plasma-gas discharge port and the diluent-gas discharge port, respectively. The former gas stream passes through the plasma generation area in the first gas passage, while the latter gas stream passes through the current detection area in the second gas passage. Since the two gas streams are basically independent of each other, their flow rates can be individually regulated with the flow controllers provided at the plasma-gas discharge port and the diluent-gas discharge port, respectively.

In the second mode, the plasma gas is introduced from the plasma-gas supply port into the first gas passage, while the diluent gas is introduced from the diluent-gas supply port into the second gas passage. Both gases are directed toward the common port functioning as the plasma-gas discharge port and the diluent-gas discharge port, to be merged with each other and discharged. Similar to the first mode, the former gas stream passes through the plasma generation area in the first gas passage, while the latter gas stream passes through the current detection area in the second gas passage. Since the two gas streams are basically independent of each other, their flow rates can be individually regulated with the flow controllers provided at the plasma-gas supply port and the diluent-gas supply port, respectively.

Thus, in the discharge current ionization current detector according to the first aspect of the present invention, although the first gas passage and the second gas passage form one continuous passage, the plasma-gas stream and the diluent-gas stream are practically separated, whereby the two gases are prevented from being mixed at least before the plasma gas passes through the plasma-gas generation area and the diluent gas passes through the current detection area. Therefore, it is possible to separately control the flow rate of the plasma gas and that of the diluent gas by using the two flow controllers. Accordingly, in both of the first and second modes, it is possible to set the flow rate of the plasma gas at an appropriate level where the plasma can be generated in a stable manner, and also optimally set the flow rate of the diluent gas so that the degree of dilution will be at an appropriate level according to the concentration of the sample in the sample gas. In this manner, the detection sensitivity can be improved without deteriorating the plasma's stability.

The present invention is particularly advantageous when the low-frequency dielectric barrier discharge is used. Although the plasma generated by this discharge process is non-equilibrium plasma and hence free from the problem of heat generation, there still remains the problem of impurities, which are released from the inner wall of conduit lines and the electrodes even at room temperature. Under this condition, increasing the flow rate of the plasma gas effectively removes the impurities, thereby enhancing the plasma's stability and improving the ionization efficiency. Meanwhile, even when the amount of sample component contained in the sample gas is extremely small, a high-current output can be obtained by setting the flow rate of the diluent gas at a sufficiently low level for creating a smooth flow of the diluent gas. In the low-frequency dielectric barrier discharge, the electric discharge necessary for the detection of sample components can occur even if the plasma gas is supplied at such a low flow rate that would cause damage to the electrodes if a normal metal-electrode discharge were used. Therefore, for example, in a field analysis or similar situation where the plasma-gas consumption should be suppressed to the lowest possible level, it is possible to appropriately perform the analysis by setting the flow rates of both the plasma gas and the diluent gas at low levels during the normal mode of the measurement, and to increase the flow rate of the diluent gas only when the measurement of a high-concentration sample is performed. In the latter measurement, if the flow rate of the plasma gas is simultaneously increased, the ionization efficiency will change, which will result in an incorrect determination of the quantity. This problem can be avoided in the present invention since the flow rate of the diluent gas can be solely increased without changing the flow rate of the plasma gas. Thus, the quantity concerned can be correctly determined.

The process of ionizing a sample by plasma excitation is primarily governed by the action of excitation light emitted from the plasma. Even if chemical species or the like produced by the plasma cannot reach the current detection area, an adequately high level of ionization efficiency can be attained as long as the excitation light emitted from the plasma generation area efficiently reaches the current detection area. Therefore, the fact that the plasma-gas stream does not reach the current detection area becomes no inhibitory factor to the sample ionization.

The discharge ionization current detector according to the first aspect of the present invention may have a configuration that can be switched between the first and second modes. More specifically, it may have a configuration in which a common supply/discharge port is provided at a connecting section of the first gas passage and the second gas passage, a plasma-gas discharge/supply port is provided at one end of the first gas passage opposing the connecting section across the plasma generation area where the plasma is generated by the plasma generator, a diluent-gas discharge/supply port is provided at one end of the second gas passage opposing the connecting section across the current detection area where the ion current is detected by the current detector, switching units for changing the gas-flow direction are respectively provided at the common supply/discharge port, the plasma-gas discharge/supply port and the diluent-gas discharge/supply port, the flow controllers are respectively provided between the plasma-gas discharge/supply port and the switching unit corresponding thereto and between the diluent-gas discharge/supply port and the switching unit corresponding thereto, and an injection-point changing unit for moving the point of injection of the sample gas into the second gas passage by the sample-gas injector is provided.

In the second mode, the dilution ratio cannot be set to extremely low levels since the diluent gas needs to be supplied at a certain flow rate to create a smooth flow of sample gas through the current detection area. By contrast, in the first mode, the flow rate of the diluent gas through the current detection area can be further decreased, so that the dilution ratio can be easily lowered. Thus, the first mode has an advantage over the second mode in terms of detection sensitivity. Therefore, it is preferable to use the first mode when the measurement is performed on a low-concentration sample. However, in the first mode, when a high-concentration sample is injected into the gas passage by the sample-gas injector and the sample is insufficiently diluted with the diluent gas, the ionization efficiency may decrease since the excitation light emitted from the plasma undergoes absorption by the sample gas and becomes dimmed before reaching the current detection area. Such a situation barely occurs in the second mode. Accordingly, it is preferable to use the second mode when the measurement is performed on a high-concentration sample. Additionally, the second mode allows the use of different kinds of gases as the plasma gas and the diluent gas.

In the discharge ionization current detector having the aforementioned configuration, it is possible to select one of the first and second modes according to the concentration range of the sample of interest, the kind of the sample, the purpose of the measurement or other conditions. This selection may be performed manually or automatically. For example, the discharge ionization current detector having the aforementioned configuration may further include a controller for conducting an operation for changing the gas-flow direction by the switching units and moving the injection point of the sample gas by the injection-point changing means.

A second aspect of the present invention aimed at solving the previously described problem is a discharge ionization current detector including: a plasma generator for generating a dielectric barrier discharge in a gas passage by a low-frequency alternating electric field to create plasma from the plasma gas; and a current detector for detecting, in the gas passage on the downstream side of the plasma generator, an ion current due to a sample component in a sample gas ionized by the action of the plasma, the discharge ionization current detector including:

a) a plasma-gas supply port for passing a plasma gas through the gas passage, the plasma-gas supply port being provided on one side of a plasma generation area where the plasma is generated by the plasma generator and opposing a current detection area where the ion current is detected by the current detector;

b) a gas-splitting discharge port for discharging a portion of the plasma gas from a space between the plasma generation area and the current detection area in the gas passage;

c) a sample-gas injector for supplying a sample gas into a section of the gas passage between the gas-splitting discharge port and the current detection area;

d) a gas discharge port provided in a section of the gas passage on the downstream side of the current detection area; and e) flow controllers respectively provided at the gas-splitting discharge port and the gas discharge port.

In the discharge ionization current detector according to the first aspect of the present invention, the flow of gas passing through the plasma generation area and the flow of gas passing through the current detection area is separated from each other. By contrast, in the discharge ionization current detector according to the second aspect of the present invention, a portion of the plasma-gas that has passed through the plasma generation area is discharged through the gas-splitting discharge port, and the remaining portion passes through the current detection area. There is no distinct separation between the flow of gas passing through the plasma generation area and the flow of gas passing through the current detection area. However, the latter system is similar to the former system in that the flow rate of the gas passing through the plasma generation area and that of the gas passing through the current detection area can be independently controlled by appropriately setting the flow rates of the two flow controllers.

As described thus far, the discharge ionization current detectors according to the first and second aspects of the present invention are both characterized in that the flow rate of the gas passing through the plasma generation area (i.e. the plasma gas) and that of the gas passing through the current detection area (i.e. the diluent gas) can be independently controlled. This feature has the following advantageous effects.

(1) The flow rate of the gas passing through the plasma generation area can be increased to enhance the plasma's stability and also improve the efficiency of ionization caused by the excitation light emitted from the plasma. Meanwhile, when the concentration of the component of interest in the sample gas is low (extremely small), the flow rate of the gas passing through the current detection area can be decreased to lower the dilution ratio and thereby improve the detection sensitivity.

(2) In a field analysis or similar situation where the gas consumption should be decreased to the lowest possible level, the flow rate of the gas passing through the plasma generation area can be lowered within a range where the plasma can be sufficiently generated. For a high-concentration sample, the flow rate of the gas passing through the current detection area can be increased to make the sample more diluted so that it can be detected within a high-linearity detection range.

(3) Only a single detector is needed to appropriately perform measurements according to the purpose and environment of the measurement, the kind and concentration of the sample concerned, or other factors. This detector can perform various measurements with the same level of accuracy and sensitivity as achieved by dedicated detectors.

DETAILED DESCRIPTION OF A PREFERRED EMBODIMENT

First Embodiment

Figure 1:
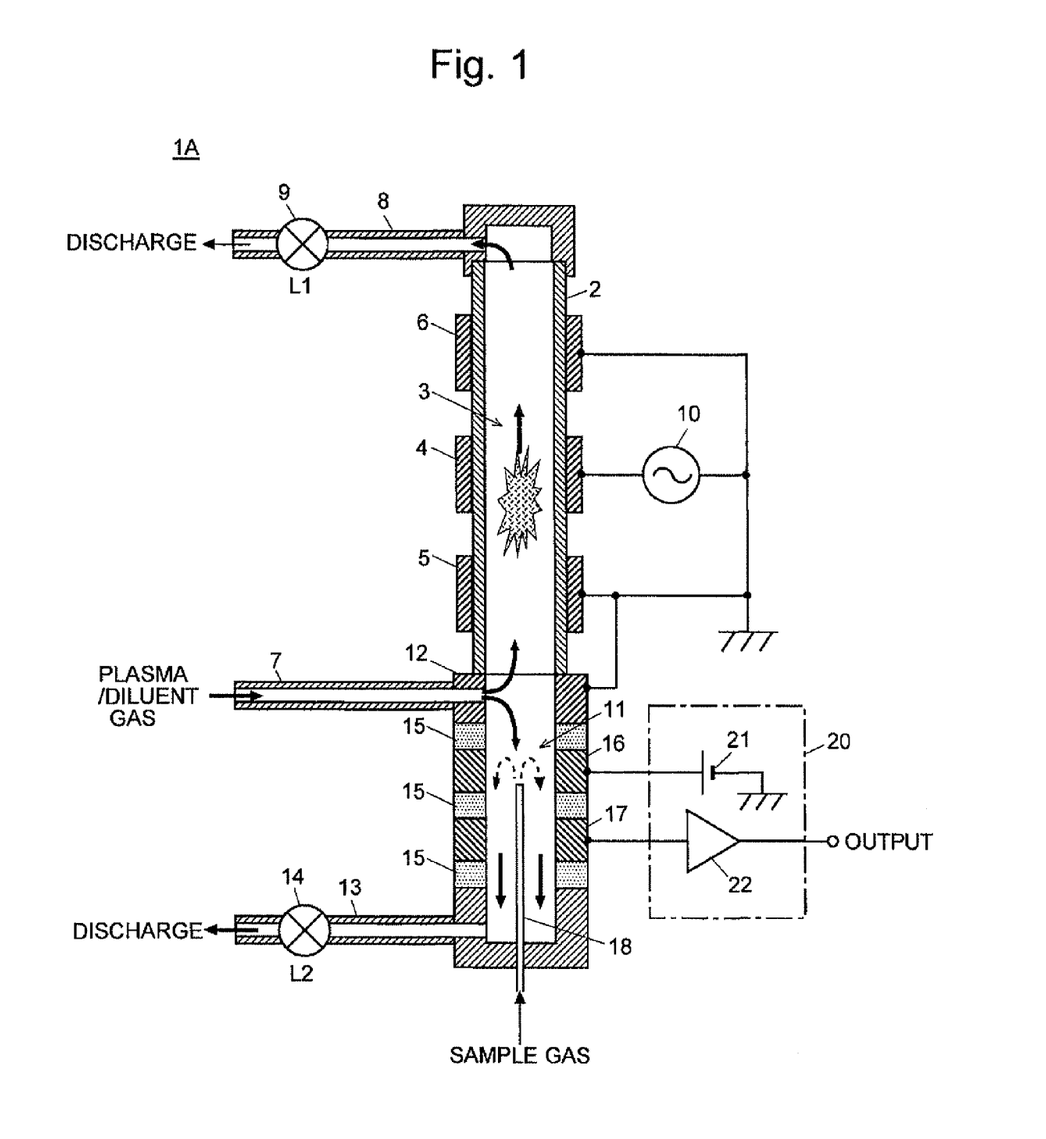
FIG. 1 is a schematic configuration diagram of a discharge ionization current detector according to one embodiment of the present invention.

A discharge ionization current detector according to one embodiment (first embodiment) of the present invention is hereinafter described with reference to FIG. 1. FIG. 1 is a schematic configuration diagram of the discharge ionization current detector according to the first embodiment.

The discharge ionization current detector 1A of the present embodiment includes a cylindrical tube 2 made of a dielectric material, such as quartz. The inner space of this tube 2 is the first gas passage 3. For example, the cylindrical tube 2 may be a quartz tube having an outer diameter of 3.9 mm. Ring-shaped plasma generation electrodes 4, 5 and 6, which are made of a metal (e.g. stainless steel or copper), are circumferentially provided at predetermined intervals on the outer wall surface of the cylindrical tube 2. According to this design, the dielectric wall of the cylindrical tube 2 between the first gas passage 3 and the plasma generation electrodes 4, 5 and 6 functions as a dielectric coating layer that covers the electrodes 4, 5 and 6, thereby enabling dielectric barrier discharge to occur.

Among the three plasma generation electrodes 4, 5 and 6, the central electrode 4 is connected to an excitation high-voltage power source 10, while the other electrodes 5 and 6 located on the both sides of the central electrode 4 are connected to ground. The structure in which the electrode 4, to which the high voltage is applied, is sandwiched between the grounded electrodes 5 and 6 prevents the plasma produced by the electric discharge from spreading toward the upstream and downstream ends of the gas stream (i.e. downwards and upwards in FIG. 1), thereby limiting the substantial plasma generation area to the space between the two plasma generation electrodes 5 and 6. The excitation high-voltage power source 10 generates a low-frequency high AC voltage. Its frequency is within a range from 1 kHz to 100 kHz, more preferably from 5 kHz to 50 kHz. The AC voltage may have any waveform, such as sine waves, rectangular waves, triangular waves or saw-tooth waves.

A recoil electrode 12, a bias electrode 16 and an ion-collecting electrode 17 are arranged in the lower portion of the cylindrical tube 2, with intervening insulators 15 made of alumina, PTFE resin or other materials. These electrodes each consist of a cylindrical body having the same inner diameter. These cylindrical bodies internally form a second gas passage 11 continuously extending from the first gas passage 3 in the cylindrical tube 2. These electrodes 12, 16 and 17 are directly exposed to the gas inside the gas passage 11. The recoil electrode 12 is a grounded electrode for preventing charged particles in the plasma from reaching the ion-collecting electrode 17. This is effective in reducing the noise and improving the S/N ratio. The bias electrode 16 is connected to a bias current power source 21 included in an ion-current detection unit 20. The ion-collecting electrode 17 is connected to a current amplifier 22, which is also included in the ion-current detection unit 20. In the second gas passage 11, the inner spaces of the bias electrode 16 and the ion-current electrode 17 with the intermediate space therebetween form the substantial current detection area.

A gas supply pipe 7 is connected to the recoil electrode 12 located at the connecting section of the first gas passage 3 and the second gas passage 11. A predetermined gas can be supplied from a gas supply source (not shown) through the gas supply pipe 7 into the two gas passages 3 and 11. A first gas-discharge pipe 8, with a first flow controller 9 provided therein, is connected to the upper end of the cylindrical tube 2, i.e. the distal end of the first gas passage 3 extending from the connection point of the gas supply pipe 7. Similarly, a second gas-discharge pipe 13, with a second flow controller 14 provided therein, is connected to the distal end of the second gas passage 11, which also extends from the connection point of the gas supply pipe 7. A sample-injecting pipe 18 with a small diameter is inserted into the second gas passage 11, through which a gas containing a sample component of interest can be supplied to a region near the connection point of the gas supply pipe 7 in the second gas passage 11.

A detecting operation of this discharge ionization current detector 1A is hereinafter described.

As indicated by the right-pointing arrow in FIG. 1, a stream of plasma gas, which also serves as the diluent gas, is supplied through the gas supply pipe 7 into the gas passages 3 and 11. The plasma gas is a kind of gas that can be easily ionized, examples of which include helium, argon, nitrogen, neon, xenon and any mixture of two or more of these elements. The flow rates of the first and second flow controllers 9 and 14 are previously set at appropriate levels. When the flow rate of the gas through the first gas discharge pipe 8 regulated with the first flow controller 9 is denoted by L1 and the flow rate of the gas through the second gas discharge pipe 13 regulated with the second flow controller 14 is denoted by L2, the flow rate of the gas supplied through the gas supply pipe 7 equals L1+L2.

As shown in FIG. 1, the plasma gas ejected from the gas supply pipe 7 is split into two streams, one stream flowing upward through the first gas passage 3 and the other stream flowing downward through the second gas passage 11. The upward stream of the plasma gas passes through the plasma generation area, to be eventually discharged through the first gas-discharge pipe 8 to the outside. On the other hand, the downward stream of the plasma gas (which herein acts as the diluent gas) merges with the sample gas supplied through the sample-injecting pipe 18 and then passes through the current detection area, to be eventually discharged through the second gas-discharge pipe 13 to the outside. Thus, the gas stream passing through the plasma generation area and the gas stream passing through the current detection area are basically independent of each other, the former having a flow rate of L1 and the latter having a flow rate of L2 (+Ls, which is the flow rate of the sample gas).

When the plasma gas is passing through the first gas passage 3 in the previously described manner, the excitation high-voltage power source 10 is energized to apply a low-frequency high AC voltage between the plasma-generating electrode 4 and each of the other electrodes 5 and 6. As a result, electric discharge occurs in the plasma generation area between the two electrodes 5 and 6 in the first gas passage 3. This electric discharge is dielectric barrier discharge since it is induced through the dielectric coating layer (the cylindrical tube 2). Due to this dielectric barrier discharge, the plasma gas flowing through the first gas passage 3 is ionized over a broad area. Thus, a cloud of plasma (i.e. atmospheric non-equilibrium micro-plasma) is created.

The atmospheric non-equilibrium micro-plasma emits excitation light, which travels through the first and second gas passages 3 and 11 to the region where the sample gas is present, and ionizes the molecules (or atoms) of a sample component in the sample gas. The resulting sample ions move to the ion-collecting electrode 17 due to the effect of a bias DC voltage applied to the bias electrode 16, and give electrons to, or receive electrons from, the electrode 17. As a result, an ion current corresponding to the amount of the generated sample ions, and hence the amount of the sample component, is fed to the current amplifier 22, which amplifies the received current to produce an output signal. In this manner, the present discharge ionization current detector 1A produces detection signals corresponding to the amount (or concentration) of the sample component contained in the injected sample gas.

As already stated, the two streams of plasma gas are independent of each other. Therefore, it is possible to set the flow rate L1 at a high level to stabilize the plasma and improve the ionization efficiency, and also adjust the flow rate L2 to a level corresponding to an appropriate dilution ratio for the concentration range of the sample of interest. Particularly, when the sample concentration is low, the flow rate L2 can be set to a low level. Then, the sample gas passing through the current detection area becomes less diluted, so that even minor components of the sample can be detected with high sensitivity. Thus, the present detector can detect sample components with high sensitivity while maintaining the stability of the plasma to achieve a high level of ionization efficiency.

However, when the concentration of the sample component in the sample gas is high, the following problem is likely to occur: The dilution of the sample gas injected through the sample-injecting pipe 18 into the second gas passage 11 does not immediately occur after the injection of the sample gas. Therefore, the sample concentration of the gas near the exit of the sample-injecting pipe 18 is rather high. The excitation light coming from the plasma directly passes through this high-concentration gas, producing a large amount of ions originating from the sample. In this situation, the concentration of the ions may fall outside the high-linearity detection range. Thus, when the sample concentration is extremely high, the operation of increasing the flow rate L2 may not be ineffective in diluting the sample, in which case the sample will be detected with a low level of linearity. To address this problem, the detector according to the second embodiment, which will be described below, is specifically designed for the detection of samples having relatively high concentrations.

Second Embodiment

Figure 2:
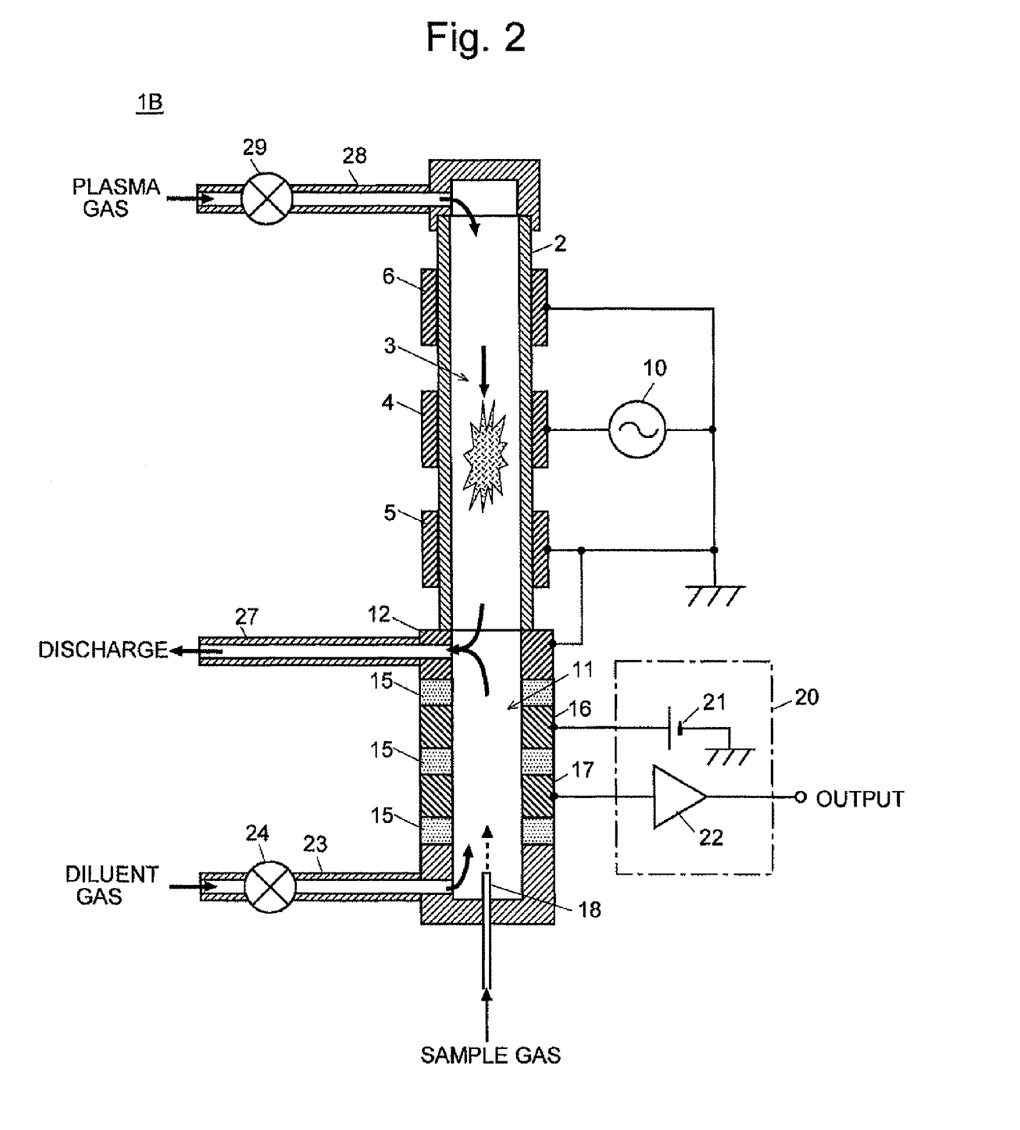
FIG. 2 is a schematic configuration diagram of a discharge ionization current detector according to another embodiment of the present invention.

FIG. 2 is a schematic configuration diagram of a discharge ionization current detector 1B according to the second embodiment of the present invention. The same components as used in the first embodiment are denoted by the same numerals, and hence no detailed explanation will be made for these components. It should be noted that the components corresponding to the gas supply pipe 7, the first gas discharge pipe 8, the first flow controller 9, the second gas discharge pipe 13 and the second flow controller 14 in the first embodiment are structurally identical to these components and yet denoted by different numerals since they have different functions. That is to say, in the discharge ionization current detector of the second embodiment, a plasma gas is supplied into the first gas passage 3 through a plasma-gas supply pipe 28 connected to the upper end of the cylindrical tube 2, and a diluent gas is supplied into the second gas passage 11 through a diluent-gas supply pipe 23 connected to the second gas passage 11 at a point lower than the ion-collecting electrode 17. The plasma-gas supply pipe 28 is provided with a first flow controller 29 for regulating the supply rate of the plasma gas. Similarly, the diluent-gas supply pipe 23 is provided with a second flow controller 24 for regulating the supply rate of the diluent gas. A gas discharge pipe 27, which is commonly used for discharging both the plasma gas and the diluent gas, is connected to a point near the connecting section of the first gas passage 3 and the second gas passage 11. Another difference of the present embodiment from the first embodiment exists in that the exit of the sample-injecting pipe 18 inserted into the second gas passage 11 is at a level lower than the ion-collecting electrode 17.

As indicated by the arrows in FIG. 2, the directions of the gas streams respectively flowing through the first gas passage 3 and the second gas passage 11 are opposite to the directions in the first embodiment; that is to say, the plasma gas flows downwards through the plasma generation area in the first gas passage 3, while the diluent gas flows upwards through the current detection area in the second gas passage 11. Both gas streams eventually merge with each other, to be discharged through the gas discharge pipe 27. Similar to the first embodiment, the flow rate L1 of the plasma gas and the flow rate L2 of the diluent gas can be independently regulated by means of the first flow controller 29 and the second flow controller 24, respectively. An important point of the present configuration exists in that the diluent gas and the sample gas are mixed together in the lower section of the second gas passage 11 before they begin to flow upward. The sample gas is adequately diluted before it reaches the upper part of the current detection area. Therefore, even if the concentration of the sample gas is high, no excessive generation of ions occurs and the ions can be detected within a high-linearity concentration range.

Additionally, the present configuration allows the use of different kinds of gases as the plasma gas and the diluent gas. For example, different kinds of plasma gases can be selectively used to change excitation energy so as to enhance the ionization efficiency for a specific compound and improve the detection sensitivity for that compound. It is also possible to use, as the diluent gas, a dopant gas (e.g. methane gas), which itself can be easily ionized by excitation. In this case, a large amount of ion current flows when no sample component is present in the sample gas, and when a sample component is introduced, the ion current decreases according to the concentration of the injected sample component. This detection mechanism is the same as the electron capture detector (ECD).

Third Embodiment

As already stated, although the detectors of the first and second embodiments have almost the same basic configuration, they have a significant difference in terms of the suitable sample-concentration range. That is to say, the first embodiment is suitable for the high-sensitivity detection of low-concentration samples but not for the detection of high-concentration samples. By contrast, the second embodiment, which is suitable for the detection of high-concentration samples, is inferior to the first embodiment in detection sensitivity since it requires the supply of a certain amount of diluent gas to create a smooth flow of gas through the second gas passage 11. To address this problem, the detector according to the third embodiment of the present invention has a mechanism for appropriately switching the passage configuration between the first embodiment and the second embodiment so as to cover a wide range of sample concentration.

Figure 3:
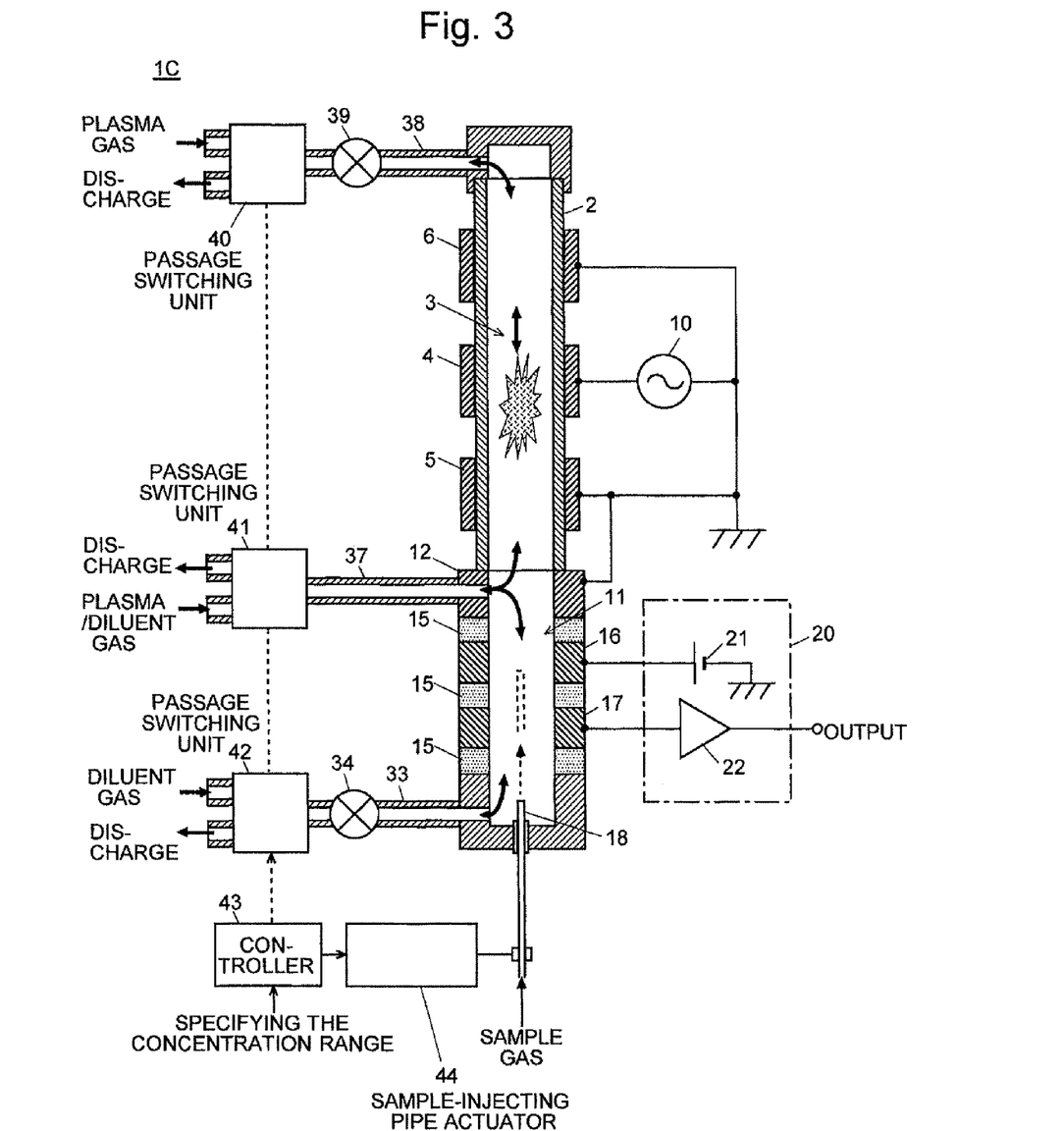
FIG. 3 is a schematic configuration diagram of a discharge ionization current detector according to still another embodiment of the present invention.

FIG. 3 is a schematic configuration diagram of a discharge ionization current detector IC according to the third embodiment. The same components as used in the first and second embodiments are denoted by the same numerals, and hence no detailed explanation will be made for these components.

A first gas supply/discharge pipe 38, one end of which is connected to the upper end of the cylindrical tube 2, is provided with a passage-switching unit 40 for connecting either a gas supply passage or a gas discharge passage to the other end of this pipe 38. A first flow controller 39 is provided between the passage-switching unit 40 and the end connected to the cylindrical tube 2. Similarly, a second gas supply/discharge pipe 33, one end of which is connected to the second gas passage 11 at a point lower than the ion-collecting electrode 17, is provided with a passage-switching unit 42 for connecting either a gas supply passage or a gas discharge passage to the other end of this pipe 33. A second flow controller 34 is provided between the passage-switching unit 42 and the end connected to the second gas passage 11. Furthermore, a third gas supply/discharge pipe 37 is connected to a point near the connecting section of the first gas passage 3 and the second gas passage 11, and either a gas supply passage or a gas discharge passage can be connected to this pipe 37 by a passage-switching unit 41. The settings of the passage-switching units 40, 41 and 42 can be synchronously changed by a controller 43. The sample-injecting pipe 18 projecting into the second gas passage 11 can be moved back and forth by a sample-injecting pipe actuator 44 within a range between the position indicated by the solid line and the position indicated by the broken line in FIG. 3.

In this discharge ionization current detector IC, for example, the concentration range of a sample of interest can be specified through an input unit (not shown). The controller 43 changes the settings of the passage-switching units 40, 41 and 42 to create a suitable passage configuration for the specified range and also changes the position of the sample-injecting pipe 18 by means of the sample-injecting pipe actuator 44. For example, when a normal range is specified, the controller 43 changes the settings of the passage-switching units 40, 41 and 42 so as to connect the upper passages of these units to the gas supply/discharge pipes 38, 33 and 37, respectively, and also moves the sample-injecting pipe 18 to the position indicated by the solid line. The configuration thus created is substantially the same as the second embodiment and hence suitable for the detection of high-concentration samples. On the other hand, when a low-concentration range for the detection of a minor component is specified, the controller 43 changes the settings of the passage-switching units 40, 41 and 42 so as to connect the lower passages of these units to the gas supply/discharge pipes 38, 33 and 37, respectively, and also moves the sample-injecting pipe 18 to the position indicated by the broken line. The configuration thus created is substantially the same as the first embodiment and hence suitable for the detection of low-concentration samples. The optimal flow rates of the flow controllers 34 and 39 for each of the two configurations can be appropriately determined beforehand.

Fourth Embodiment

Figure 4:
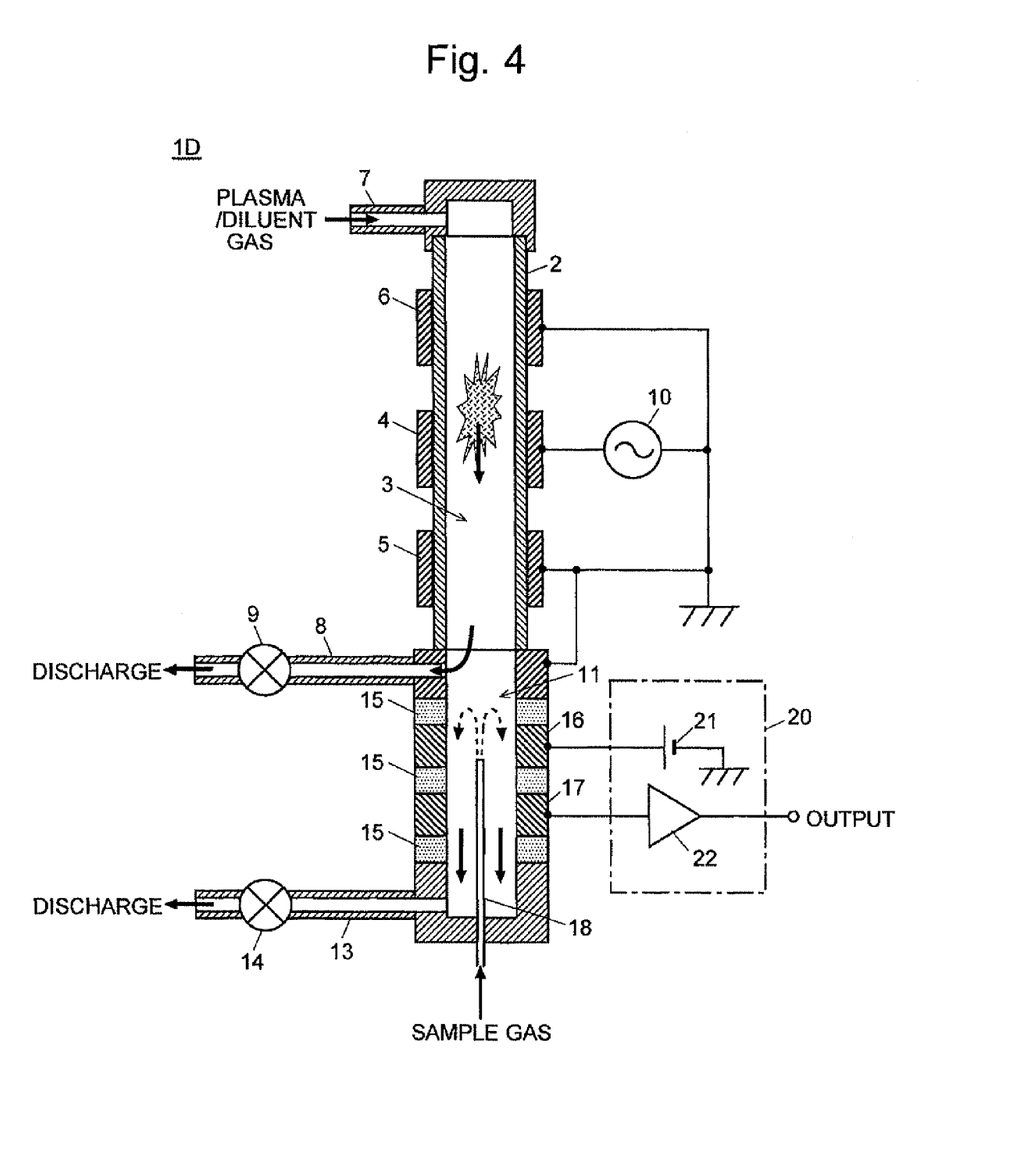
FIG. 4 is a schematic configuration diagram of a discharge ionization current detector according to still another embodiment of the present invention.

A discharge ionization current detector ID according to still another embodiment of the present invention (the fourth embodiment) is hereinafter described with reference to FIG. 4.

The configuration of the fourth embodiment can be created by transposing the connection points of the gas supply pipe 7 and the first gas discharge pipe 8 of the discharge ionization current detector 1A of the first embodiment. In this configuration, the plasma gas, which also serves as the diluent gas, flows downwards through the first gas passage 3. When the flow rate of the gas through the first gas discharge pipe 8 regulated with the first flow controller 9 is denoted by L1 and the flow rate of the gas through the second gas discharge pipe 13 regulated with the second flow controller 14 is denoted by L2, the flow rate of the gas passing through the plasma generation area in the first gas passage 3 equals L1+L2. That is to say, the flow rate of the gas passing through the plasma generation area in the present embodiment exceeds the level of the first embodiment by an amount corresponding to the diluent gas.

At the lower end of the first gas passage 3, a portion of the plasma gas corresponding to the flow rate L1 is split into the first gas discharge pipe 8 and discharged to the outside. The remaining portion of the plasma gas having a flow rate of L2 acts as a diluent gas, which becomes mixed with the sample gas and flows through the current detection area. In the present case, the gas stream flowing through the first gas passage 3 and the gas stream flowing through the second gas passage 11 are not independent of each other; if the flow rate L2 is changed to vary the dilution ratio, the flow rate L1 of the gas passing through the plasma generation area also changes. Despite this dependency, it is possible to appropriately control the flow rates by the flow controllers 9 and 14 so that the flow rate of the gas passing through the plasma generation area and that of the gas passing through the current detection area are each adjusted to a desired level. Thus, the same effects as in the first through third embodiments can be achieved.

It should be noted that the previously described embodiments are mere examples of the present invention. Any change, modification or addition appropriately made within the spirit of the present invention will naturally fall within the scope of claims of the present patent application.

What is claimed is:
1. A discharge ionization current detector comprising:
a first gas passage for passing a plasma gas therethrough;
a plasma generator for generating a dielectric barrier discharge in the first gas passage by a low-frequency alternating electric field to create plasma from the plasma gas;
a second gas passage continuously extending from the first gas passage;
a current detector for detecting, in the second gas passage, an ion current due to a sample component in a sample gas ionized by an action of the plasma,
a plasma-gas supply port and a plasma-gas discharge port for passing the plasma gas through the first gas passage, the plasma-gas supply port being provided in the first gas passage on one side of a plasma generation area where the plasma is generated by the plasma generator, and the plasma-gas discharge port being provided on another side downstream from the plasma generation area;
a sample-gas injector for supplying a sample gas into the second gas passage;

a diluent-gas supply port and a diluent-gas discharge port for passing the sample gas through the second gas passage after diluting the sample gas, the diluent-gas supply port being provided in the second gas passage on one side of a current detection area where the ion current is detected by the current detector, and the diluent-gas discharge port being provided on another side downstream from the current detection area; and flow controllers respectively provided at the plasma-gas supply port and the diluent-gas supply port to control separately the flow rate of the plasma gas and the flow rate of the diluent gas.

2. The discharge ionization current detector according to claim 1, wherein a common port functioning as both the plasma-gas supply port and the diluent-gas supply port is provided at a connecting section of the first gas passage and the second gas passage; and the flow controllers are respectively provided at the plasma-gas discharge port and the diluent-gas discharge port.

3. The discharge ionization current detector according to claim 1, wherein a common port functioning as both the plasma-gas discharge port and the diluent-gas discharge port is provided at a connecting section of the first gas passage and the second gas passage.

4. The discharge ionization current detector according to claim 1, wherein a common supply/discharge port is provided at a connecting section of the first gas passage and the second gas passage; a plasma-gas discharge/supply port is provided at one end of the first gas passage opposing the connecting section across the plasma generation area where the plasma is generated by the plasma generator; a diluent-gas discharge/supply port is provided at one end of the second gas passage opposing the connecting section across the current detection area where the ion current is detected by the current detector; switching units for changing a gas-flow direction are respectively provided at the common supply/discharge port, the plasma-gas discharge/supply port and the diluent-gas discharge/supply port; the flow controllers are respectively provided between the plasma-gas discharge/supply port and the switching unit corresponding thereto and between the diluent-gas discharge/supply port and the switching unit corresponding thereto; and an injection-point changing unit for moving the point of injection of the sample gas into the second gas passage by the sample-gas injector is provided.

5. The discharge ionization current detector according to claim 4, further comprising a controller for conducting an operation for changing the gas-flow direction by the switching units and moving the injection point of the sample gas by the injection-point changing means.

6. A discharge ionization current detector comprising:
a plasma generator for generating a dielectric barrier discharge in a gas passage by a low-frequency alternating electric field to create plasma from the plasma gas;
a current detector for detecting, in the gas passage on a downstream side of the plasma generator, an ion current due to a sample component in a sample gas ionized by an action of the plasma;
a plasma-gas supply port for passing a plasma gas through the gas passage, the plasma-gas supply port being provided on one side of a plasma generation area where the plasma is generated by the plasma generator and opposing a current detection area where the ion current is detected by the current detector;
a gas-splitting discharge port for discharging a portion of the plasma gas from a space between the plasma generation area and the current detection area in the gas passage;
a sample-gas injector for supplying a sample gas into a section of the gas passage between the gas-splitting discharge port and the current detection area;
a gas discharge port provided in a section of the gas passage on a downstream side of the current detection area; and
flow controllers respectively provided at the gas-splitting discharge port and the gas discharge port.

7. The discharge ionization current detector according to claim 1, wherein the plasma-gas discharge port provided downstream from the plasma generation area and the diluent-gas discharge port provided upstream from the current detection area are a same gas discharge pipe.

8. A discharge ionization current detector comprising:
a first gas passage for passing a plasma gas therethrough;
a plasma generator for generating a dielectric barrier discharge in the first gas passage by a low-frequency alternating electric field to create plasma from the plasma gas;
a second gas passage continuously extending from the first gas passage;
a current detector for detecting, in the second gas passage, an ion current due to a sample component in a sample gas ionized by an action of the plasma;
a plasma-gas supply port and a gas discharge port for passing the plasma gas through the first gas passage, the plasma-gas supply port being provided in the first gas passage on one side of a plasma generation area where the plasma is generated by the plasma generator, and the gas discharge port being provided on another side downstream from the plasma generation area;
a sample-gas injector for supplying the sample gas into the second gas passage;
a diluent-gas supply port and the gas discharge port for passing the sample gas through the second gas passage after diluting the sample gas, the diluent-gas supply port being provided in the second gas passage on one side of a current detection area where the ion current is detected by the current detector, and the gas discharge port being provided on another side downstream from the current detection area; and
flow controllers respectively provided at the plasma-gas supply port and the diluent-gas supply port to control separately the flow rate of the plasma gas and the flow rate of the diluent gas.

9. The discharge ionization current detector according to claim 8, wherein the gas discharge port is provided at a connecting section of the first gas passage and the second gas passage.

\* \* \* \* \*